(12) United States Patent
Stilz et al.

(10) Patent No.: US 6,294,562 B1
(45) Date of Patent: Sep. 25, 2001

(54) SALTS OF ETHYL 3-(2-(4-(4-AMINO-IMINO-METHYL)PHENYL)-4-METHYL-2,5-DIOXO-IMIDAZOLIDIN-1-YL)ACETYLAMINO)-3-PHENYLPROPIONATE

(75) Inventors: Hans Ulrich Stilz; Gerhard Beck, both of Frankfurt; Manfred Radau, Kelkheim, all of (DE)

(73) Assignee: Hoechst Aktiengesellschaft, Frankfurt am Main (DE)

( * ) Notice: Subject to any disclaimer, the term of this patent is extended or adjusted under 35 U.S.C. 154(b) by 0 days.

(21) Appl. No.: 09/301,907

(22) Filed: Apr. 29, 1999

Related U.S. Application Data

(63) Continuation of application No. 08/868,682, filed on Jun. 4, 1997, now abandoned.

(30) Foreign Application Priority Data

Jun. 5, 1996 (DE) .............................. 196 22 489

(51) Int. Cl.⁷ .................... A61K 31/4166; C07D 233/76
(52) U.S. Cl. ........................ 514/391; 548/319.5
(58) Field of Search .......................... 548/319.5; 514/391

(56) References Cited

U.S. PATENT DOCUMENTS

| 5,389,614 | 2/1995 | Konig et al. ........................ 514/18 |
| 5,397,796 | 3/1995 | Zoller et al. ....................... 514/389 |
| 5,424,293 | 6/1995 | Zoller et al. ........................ 514/20 |
| 5,658,935 | 8/1997 | Klingler et al. .................... 514/359 |
| 5,703,050 | 12/1997 | Klingler et al. ..................... 514/18 |
| 5,939,556 | 8/1999 | Zoller et al. ..................... 548/320.1 |
| 5,981,492 | 11/1999 | Zoller et al. ........................ 514/20 |

FOREIGN PATENT DOCUMENTS

| 95/14008 | 5/1995 | (WO) . |
| 96/33976 | 10/1996 | (WO) . |

*Primary Examiner*—Patricia L. Morris
(74) *Attorney, Agent, or Firm*—Perman & Green, LLP

(57) ABSTRACT

The present invention relates to ethyl 3-(2-(4-(4-(amino-imino-methyl)-phenyl)-4-methyl-2,5-dioxoimidazolidin-1-yl)acetylamino)-3-phenylpropionate salts of the formula I,

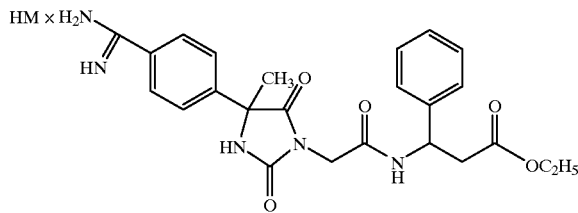

(I)

in which HM is maleic acid, and to their physiologically tolerated salts, thereof, to processes for their preparation and to their use in pharmaceuticals.

4 Claims, No Drawings

SALTS OF ETHYL 3-(2-(4-(4-AMINO-IMINO-METHYL)PHENYL)-4-METHYL-2,5-DIOXO-IMIDAZOLIDIN-1-YL)ACETYLAMINO)-3-PHENYLPROPIONATE

This appln is a continuation of Ser. No. 08/868,682 filed Jun. 4, 1997 abnd.

Salts of ethyl 3-(2-(4-(4-(amino-imino-methyl)phenyl)-4-methyl-2,5-dioxo-imidazolidin-1-yl)acetylamino)-3-phenylpropionate

SUMMARY OF THE INVENTION

The present invention relates to ethyl 3-(2-(4-(4-(amino-imino-methyl)-phenyl)-4-methyl-2,5-dioxoimidazolidin-1-yl)acetylamino)-3-phenyl-propionate salts of the formula I, (I)

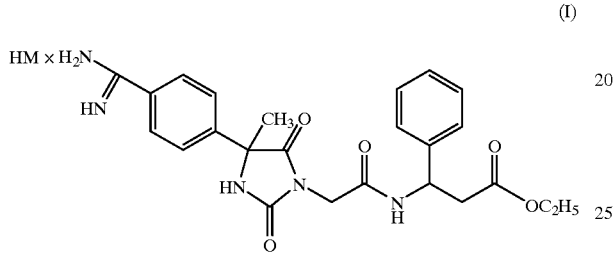

in which HM is maleic acid, and to their physiologically tolerated salts, to processes for their preparation and to their use in pharmaceuticals.

STATE OF THE ART

Ethyl 3-(2-(4-(4-(amino-imino-methyl)phenyl)-4-methyl-2,5-dioxo-imidazolidin-1-yl)acetyiamino)-3-phenyipropionate hydrochlorides and their pharmacological properties have already been described in PCT application PCT/EP94/03491 (WO-A-95/14008). However, the hydrochloride salts of ethyl (S)-3-(2-((S)-4-(4-(amino-imino-methyl)phenyl)-4-methyl-2,5-dioxoimidazolidin-1-yl) acetylamino)-3-phenylpropionate, of ethyl (R)-3-(2-((R)-4-(4-(amino-imino-methyl)phenyl)-4-methyl-2,5-dioxo-imidazolidin-1-yl)acetylamino)-3-phenylpropionate, of ethyl (S)-3-(2-((R)-4-(4-(amino-imino-methyl) phenyl)-4-methyl-2,5-dioxoimidazolidin-1-yl)-acetylamino)-3-phenylpropionate and of ethyl (R)-3-(2-((S)-4-(4-(amino-imino-methyl) phenyl)-4-methyl-2,5-dioxoimidazolidin-1-yl)acetylamino)-3-phenylpropionate suffer from the disadvantage that they are amorphous and cannot be obtained in the crystalline state. The above hydrochloride salts cannot, therefore, be purified by crystallization and can consequently scarcely be used as active compounds in pharmaceuticals, for whose constituents the legislator stipulates precisely defined degrees of purity, and as target products in the industrial synthesis of the pharmacologically active substances, in the processes for isolating and purifying which conditions have to be adhered to which are likewise precisely defined by the legal guidelines. Furthermore, on the basis of their physical and handling properties, the amorphous hydrochloride salts are not well suited for the galenic production of pharmaceutical preparations such as tablets.

The object of the present invention is, therefore, to prepare the ethyl 3-(2-(4-(4-(amino-imino-methyl)phenyl)-4-methyl-2,5-dioxoimidazolidin- -yl)-acetylamino)-3-phenylpropionates in a suitable, nonhygroscopic form, which makes it possible to adhere with ease to the degrees of purity required and meet the demands associated with industrial synthesis, as well as the galenic demands.

DETAILED DESCRIPTION

This object is achieved, surprisingly, by preparing the maleic acid salts of the ethyl 3-(2-(4-(4-(amino-imino-methyl)phenyl)-4-methyl-2,5-dioxo-imidazolidin-1-yl) acetylamino)-3-phenylpropionates, in particular the salts, which contain these ethyl esters and maleic acid in salt form (i.e. in form of an acid addition salt) in a molar ratio of approx. 1:1.

The present invention consequently relates to ethyl 3-(2-(4-(4-(amino-imino-methyl) phenyl)-4-methyl-2,5-dioxoimidazolidin-1-yl)-acetylamino)-3-phenylpropionate salts of the formula I, (I)

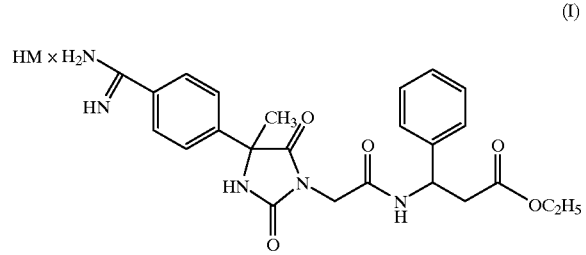

in which HM is maleic acid, in all stereoisomeric forms and mixtures thereof in any ratios, and to the physiologically tolerated salts thereof.

The compounds of the formula I are crystalline and nonhygroscopic and consequently possess advantages which it was not possible to foresee. They can be crystallized under defined conditions and be purified by recrystallization and are suitable for use in pharmaceuticals and for the galenic preparation of drug forms.

The present invention encompasses all the stereoisomers of the compounds of the formula 1, that is the isomer having an (S) configuration at the chiral center in the imidazolidine ring and an (S) configuration at the chiral center in the propionic acid unit, the isomer having an (R) configuration at the chiral center in the imidazolidine ring and an (S) configuration at the chiral center in the propionic acid unit, the isomer having an (S) configuration at the chiral center in the imidazolidine ring and an (R) configuration at the chiral center in the propionic acid unit and the isomer having an (R) configuration at the chiral center in the imidazolidine ring and an (R) configuration at the chiral center in the propionic acid unit. A preferred form is the isomer having an (S) configuration at the chiral center in the imidazolidine ring and an (S) configuration at the chiral center in the propionic acid unit, that is the ethyl (S)-3-(2-((S)-4-(4-(amino-imino-methyl)phenyl)-4-methyl-2,5-dioxoimidazolidin-1-yl)acetylamino)-3-phenyl-propionate salt of the formula Ia,

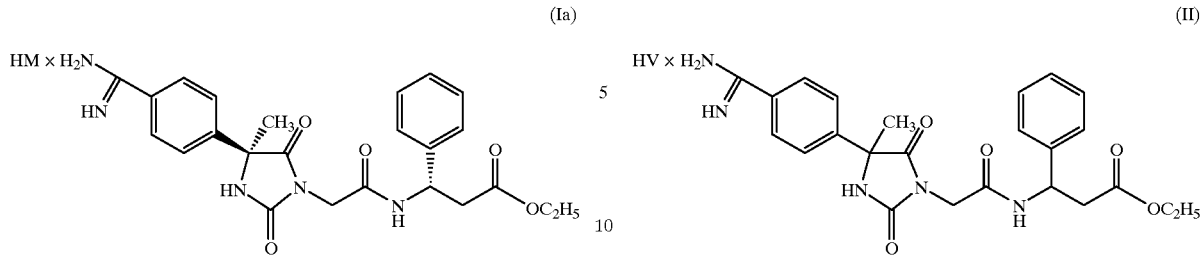

(Ia)

in which HB is maleic acid, and the physiologically tolerated salts thereof.

The present invention also encompasses all mixtures of two or more stereoisomers of the formula I in any quantity ratios.

In the novel compounds of the formula I, which contain ethyl 3-(2-(4-(4-(amino-imino-methyl) phenyl)-4-methyl-2, 5-dioxoimidazolidin-1-yl)-acetylamino)-3-phenylpropionate and maleic acid in a molar ratio of approx. 1:1, one of the two COOH groups of maleic acid is neutralized by the basic amidino group and is present in salt form, that is as negatively charged carboxylate group (after protonation by the maleic acid the amidino group in the ethyl ester is then present as positively charged amidinium group). The second of the two COOH groups of the maleic acid can be present, in the novel compounds, in acid form, that is as a COOH group, or it can be present in salt form, that is as a carboxylate group. The present invention relates both to the hydrogen maleates, in which there is still present a COOH group and which are preferred, and to the physiologically tolerated salts which are derived therefrom and which are formed from them with organic or inorganic bases.

In this context, physiologically tolerated salts are, in particular, pharmaceutically utilizable or nontoxic salts. Cations which may be present in these salts are derived, for example, from alkali metals and alkaline earth metals such as sodium, potassium, magnesium or calcium, from ammonia or from physiologically tolerated organic amines such as triethylamine, ethanolamine or tris(2-hydroxyethyl)amine. The salts of the compounds of the formula I can be obtained directly in the preparation process which is described below by employing, for example, suitable salts of maleic acid in this process or by adding suitable bases. However, the salts can also be obtained by treating initially prepared hydrogen maleates of the formula I, in which a COOH group is still present, with suitable bases, for example alkali metal or alkaline earth metal hydroxides, carbonates or hydrogen carbonates, alkaline earth metal oxides or amines. In this context, the COOH groups can either be converted completely, or only partially, into the salt form. The extent to which such a salt formation is carried out depends, for example, on the pH which is sought in association with the intended use. The conversion of free COOH groups once again completely or only partially—into the salt form can also be effected only at the time when hydrogen maleates of the formula I are employed together with basic substances in the production of pharmaceutical preparations.

The compounds of the formula I can be prepared by carrying out an anion exchange with maleic acid and/or maleates using compounds of the formula II, (II)

in which HV is any inorganic or organic acid which is different from maleic acid, in accordance with customary methods which are known to the skilled person. Examples of acids of the formula HV are hydrochloric acid, hydrobromic acid, sulfuric acid, phosphoric acid, acetic acid, propionic acid or methanesulfonic acid. Examples of compounds of the formula II are the compounds of the formulae IIa and IIb,

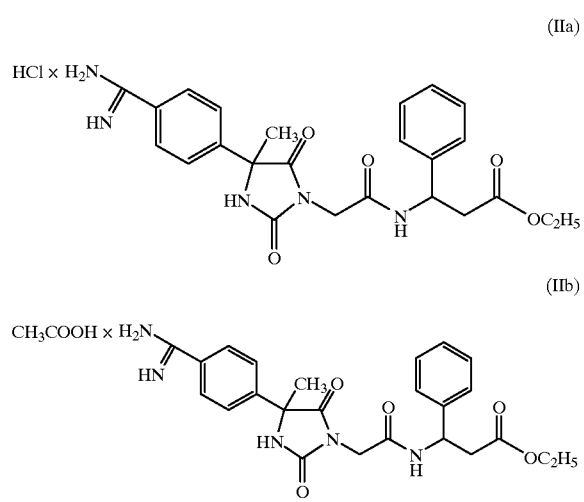

(IIa)

(IIb)

in which HV in the formula II is hydrochloric acid and acetic acid, respectively. The starting compounds of the formula II can be prepared as described, by way of example, for the hydrochloride (salt with hydrochloric acid) or for the salt with acetic acid in PCT applications PCT/EP94/03491 and PCT/EP96/01572 (WO-A-96/33976). In this respect, the content of PCT applications PCT/EP94/03491 and PCT/EP96/01 572 is, in its entirety, a constituent part of the present disclosure. Sodium salts, lithium salts, potassium salts and ammonium salts of maleic acid, or salts of maleic acid with organic ammonium cations, can, for example, be employed as maleates in the anion exchange. Preference is given to employing maleic acid.

For the anion exchange, a solution of compounds of the formula II can, for example, be chromatographed through an ion-exchange material which is loaded with maleic acid. Examples of suitable solvents for this purpose are water, alcohols such as methanol, ethanol, butanol or i-propanol, and mixtures of these solvents, for example water/alcohol mixtures. Commercially available anion-exchange materials can be employed, which materials are initially converted into the maleic acid form using the customary procedure or, respectively, regenerated into this form in the case of repeated use. The anion exchange is normally carried out at temperatures of from −10 to 40° C., in particular of from −5 to 30° C., preferably of from 0 to 25° C. The desired product can then, if desired after concentrating, be crystallized from the eluate of the ion-exchange chromatography, for example by means of cooling and/or precipitating, and be isolated by filtration or centrifugation. For the anion exchange, compounds of the formula II can also, for example, be brought into contact with maleic acid and/or maleates in a solvent. In this context, a solvent is also to be understood as being mixtures of two or more solvents. Examples of suitable solvents are water, alcohols, for example those having from 1 to 8 carbon atoms, in particular those having from 1 to 6 carbon atoms, preferably those having from 1 to 4 carbon atoms, ethers, such as dioxane, tetrahydrofuran, ethylene glycol monomethyl ether, ethylene glycol dimethyl ether, diethylene glycol monomethyl ether and diethylene glycol dimethyl ether, ketones, such as acetone or butanone, nitriles, such as acetonitrile, dimethylformamide, dimethyl sulfoxide, and mixtures of these solvents, for example mixtures of water and alcohols. Examples of alcohols which can be employed are methanol, ethanol, i- and n-propanol, n-, i-, sec- and tert-butanol, n-, i-, sec- and tert-pentanol, n-hexanol, 2-ethylbutanol, 2-ethylhexanol, isooctyl alcohol, cyclopentanol, methyicyclohexanol (mixture) or benzyl alcohol.

In this procedure, the molar ratio compound of the formula II: maleic acid or maleate is normally from 1:1 to 1:10, preferably from 1:1 to 1:2, particularly preferably approx. 1:1. The compounds of the formula II can be initially introduced and the maleic acid or the maleates, or mixtures of maleic acid and maleate, be added, or vice versa, and both components can also be metered simultaneously into the reaction vessel. While the components can be brought into contact in the form of solutions, it can, depending on the manner in which the anion exchange is performed, also be advantageous to initially introduce suspensions and/or to add suspensions or solids. The anion exchange is normally carried out at temperatures of from −10 to 40° C., in particular of from −5 to 30° C., preferably of from 0 to 25° C. For isolation, the resulting maleic acid salt can, if desired after concentrating, be crystallized out, for example by means of cooling and/or precipitating, and be separated off by means of filtration or centrifugation. Depending on the requirements, it can then additionally be washed and, if desired, be subjected to further purification, for example by means of recrystallization or digestion.

In a preferred process for preparing the novel maleic acid salts of the formula I, the acetic acid salts of the formula IIb are employed as the starting compounds. In this connection, particular preference is given to bringing the salt into contact with maleic acid in a solvent.

In a preferred procedure, the compounds of the formula II which are employed in the anion exchange may be obtained by the following route. Compounds of the formula III, (III)

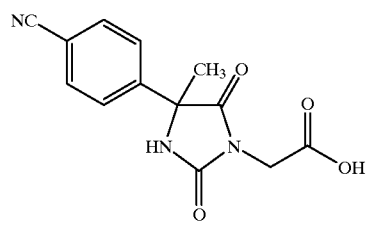

which can be prepared in accordance with the instructions given in PCT applications PCT/EP94/03491 and PCT/EP96/01572, can, in the presence of water-binding agents, such as dicyclohexylcarbodiimide (DCC), O-((cyano (ethoxycarbonyl)methylene)amino)-N,N,N',N'-tetramethyluronium tetrafluoroborate (TOTU) or propyiphosphonic anhydride (PPA), be coupled, under the conditions which are customary for such reactions, with compounds of the formula IV, (IV)

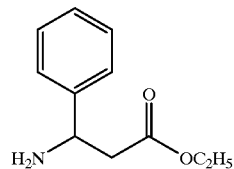

which can be prepared in accordance with methods described in the literature (see, for example, E. Juaristi, D. Quintana, J. Escalante, Aldrichimica Acta, Vol. 27, No.1, 1994, 3–11; D. C. Cole, Tetrahedron, Vol. 50, 1994, 9517–9582), to give the compounds of the formula V.

(V)

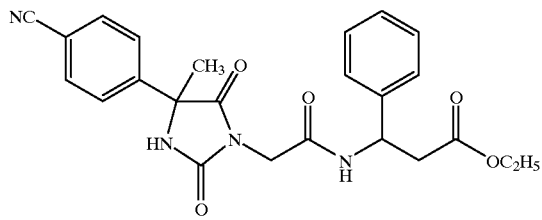

In this context, the (R) configuration or the (S) configuration can in each case be present at the chiral centers in the imidazolidine ring and in the propionic acid unit of the compounds of the formulae III and IV and V. The compounds of the formulae III and IV can be employed in the form of pure stereoisomers (enantiomers) or in the form of stereoisomeric mixtures, that is, for example, in racemic form or in optically active form.

The compounds of the formula V can be converted, for example in accordance with the customary methods for converting nitriles into amide oximes in a suitable solvent, for example in an alcohol such as methanol or ethanol, with hydroxylamine or with a hydroxylammonium salt and a base, for example a tertiary amine or an alkali metal hydroxide, carbonate or hydrogen carbonate, into the compounds of the formula VI (VI)

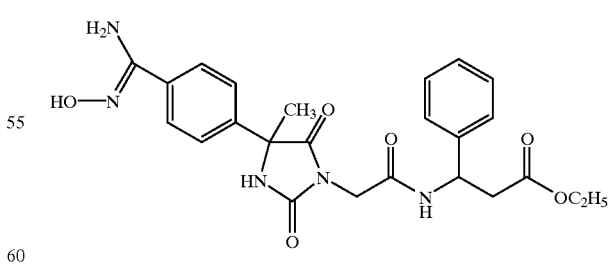

which can then be converted into the compounds of the formula II by reduction under customary conditions, for example by hydrogenation with hydrogen in the presence of metal catalysts, and by addition of the acid of the formula HV, in particular by hydrogenation in the presence of the acid of the formula HV. Precious metal catalysts, such as palladium on charcoal, can, for example, be used as metal catalysts in a hydrogenation, which can be carried out under atmospheric pressure or, preferably, under elevated pressure. For the preferred preparation of the compounds of the formula IIb, hydrogenation can, for example, be effected, in this context, in a suitable solvent in the presence of acetic acid or also in acetic acid as the solvent.

The pharmacological properties of the compounds of the formula I are unaffected by the fact that they are maleic acid salts. Like the corresponding hydrochlorides, for example, the novel compounds of the formula I are able to inhibit the cell/cell adhesion which is based on the interaction of Arg-Gly-Asp-containing proteins, such as fibronectin, fibrinogen or the von Willebrand factor, with the so-called integrins. Integrins are transmembrane glycoproteins, receptors for Arg-Gly-Asp-containing cell matrix proteins (E. Ruoslahti and M. D. Pierschbacher, Science 238 (1987) 491–497; D. R. Phillips, I. F. Charo, L. V. Parise and L. A. Fitzgerald, Blood 71 (1988) 831–843). In addition, they inhibit the binding of other adhesive proteins, such as vitronectin, collagen and laminin, to the corresponding receptors on the surface of various cell types. In particular, the novel compounds of the formula I inhibit thrombocyte aggregation and are suitable for preventing thromboses. Furthermore, the compounds of the formula I inhibit the metastasis of carcinoma cells. The present invention also relates to the use of the compounds of the formula I, and/or of their physiologically tolerated salts, for these purposes, and also to their use for preparing pharmaceuticals for inhibiting thrombocyte aggregation, for preventing thromboses or for inhibiting the metastasis of carcinoma cells.

The compounds of the formula I, and their physiologically tolerated salts, can be administered to animals, preferably to mammals, and in particular to humans, as pharmaceuticals, on their own, in mixtures with each other or in the form of pharmaceutical preparations which permit enteral or parenteral use and which comprise, as the active constituent, an effective dose of at least one compound of the formula I, or of a physiologically tolerated salt thereof, in addition to customary, pharmaceutically unobjectionable carrier and auxiliary substances. The present invention also relates to the compounds of the formula I, and their physiologically tolerated salts, for use as pharmaceuticals, as well as to pharmaceutical preparations which comprise one or more compounds of the formula I, and/or one or more physiologically tolerated salts thereof, as the active compound, together with pharmaceutically acceptable carrier and auxiliary substances and, optionally, one or more other pharmacological active compounds in addition. Such pharmaceutical preparations normally comprise from about 0.5 to 90% by weight of the compounds of the formula I, or of physiologically tolerated salts thereof.

The pharmaceuticals may be administered orally, for example in the form of pills, tablets, film tablets, coated tablets, granules, hard and soft gelatin capsules, solutions, syrups, emulsions or suspensions. However, administration may also take place rectally, for example in the form of suppositories, or parenterally, for example in the form of injection solutions, infusion solutions, microcapsules or rods, percutaneously, for example in the form of ointments or tinctures, or in some other way, for example in the form of nasal sprays or aerosol mixtures.

The pharmaceutical preparations are produced in a manner known per se, with pharmaceutically inert inorganic and/or organic carrier substances and auxiliary substances being used and these latter being brought, together with the active compounds, into the desired form for administration.

For the preparation of pills, tablets, coated tablets and hard gelatin capsules, use can be made, for example, of lactose, corn starch or derivatives thereof, talc, stearic acid or its salts, etc. Examples of carrier substances for soft gelatin capsules and suppositories are fats, waxes, semisolid and liquid polyols, natural or hardened oils, etc. Examples of suitable carrier substances for preparing solutions and syrups are water, sucrose, invert sugar, glucose, polyols, etc. Suitable carrier substances for preparing injection solutions are water, alcohols, glycerol, polyols, vegetable oils, etc. Suitable carrier substances for microcapsules, implants or rods are mixed polymers of glycolic acid and lactic acid.

In addition to the active compounds and carrier substances, the pharmaceutical preparations can also comprise auxiliary substances, such as fillers, disintegrants, binders, glidants, wetting agents, stabilizers, emulsifiers, preservatives, sweeteners, dyes, flavorants or aromatizing agents, thickeners, diluents or buffering substances, and, in addition, solvents or solubilizing agents or agents for achieving a slow-release effect, and also salts for altering the osmotic pressure, coating agents or antioxidants. They can also comprise two or more compounds of the formula I, and/or their physiologically tolerated salts, and one or more other therapeutically active compounds in addition.

Examples of such other therapeutically active substances are blood flow-promoting agents, such as dihydroergocristine, nicergoline, nicotinic acid and its esters, bencyclane, naftidrofuryl, prostacyclin derivatives and PGEI derivatives; antianginal compounds, such as isosorbide dinitrate, isosorbide mononitrate, glycerol nitrate, molsidomine, nifedipine and verapamil; and β-blockers, such as propranolol, oxprenolol, atenolol, metoprolol and penbutolol. In addition to this, the compounds can be combined with ACE inhibitors, such as captopril, ramipril, enalapril, lisinopril and trandolapril, inhibitors of thrombocyte function, such as acetylsalicylic acid, ticlopidine and clopidogrel, and inhibitors of blood coagulation, such as heparin and low molecular weight heparins.

The dose can vary within wide limits and is to be adjusted to the particular circumstances in each individual case. In general, in the case of oral administration, a daily dose of from about 0.1 to 5 mg/kg, preferably of from 0.3 to 3 mg/kg, in particular of from 0.5 to 2 mg/kg of body weight is appropriate for achieving effective results. In the case of intravenous administration, the daily dose is in general from about 0.01 to 0.6 mg/kg, preferably from 0.05 to 0.3 mg/kg, in particular from 0.05 to 0.1 mg/kg of body weight. In particular when administering relatively large quantities, the daily dose can be subdivided into several, for example 2, 3 or 4, subdose administrations. Where appropriate, it may be necessary, depending on the individual response, to deviate, in an upward or downward direction, from the given daily dose. Pharmaceutical preparations normally comprise from 0.2 to 500 mg, preferably from 1 to 200 mg, in particular from 10 to 100 mg, of active compound of the formula I, or of salts thereof, per dose.

The novel compounds can, for example, be employed in controlling or preventing diseases of the cardiovascular system, diseases of the coronary vascular system or the cerebrovascular system, or peripheral arterial diseases. They are used acutely when there is danger of a thrombosis and chronically in the prevention of arteriosclerosis and thrombosis, for example in the therapy and prophylaxis of arterial vascular diseases, as in the case of acute myocardial infarction, secondary prevention of myocardial infarction, reocclusion prophylaxis following lysis and dilatation (PTCA), unstable angina pectoris, transitory ischemic attacks, stroke, coronary bypass operations including reocclusion prophylaxis in association with a bypass, pulmonary embolism, peripheral arterial occlusion disease and dissecting aneurysm; furthermore in the therapy of venous or microcirculatory vascular diseases, such as deep vein thrombosis, disseminated intravascular coagulation, postoperative and postpartum trauma, surgical or infectious shock and septicemia, or in diseases involving hyperreactive thrombocytes, thrombotic thrombocytopenic purpura, preeclampsia and premenstrual syndrome, or in association with dialysis or extracorporeal circulation; an additional use is also that during cancer operations and prophylactically in association with cancer. The use of novel compounds of the formula I, and/or their physiologically tolerated salts, in the treatment or prophylaxis of these diseases is part of the subject-matter of the present invention, as is their use for preparing pharmaceuticals for the treatment or prophylaxis or said diseases. In particular, the invention relates to their use for preparing pharmaceuticals for the treatment or prevention of diseases of the coronary vascular system or the cerebrovascular system, of peripheral arterial diseases or of venous or microcirculatory vascular diseases, and also their use for preparing pharmaceuticals which are employed in association with dialysis or extracorporeal circulation.

The compounds of the formula I are tested for their inhibitory effect in blood platelet aggregation and in the adherence of fibrinogen to blood platelets (use is made of gel-filtered blood platelets from human donor blood which are activated with ADP or thrombin), and for their in vivo effect in the inhibition of thrombocyte aggregation and in thrombosis inhibition.

EXAMPLES

All the products were identified by means of mass spectra and NMR spectra.

Example 1

Ethyl (S)-3-(2-((S)-4-(4-(amino-imino-methyl)phenyl)-4-methyl-2,5-dioxo-imidazolidin-1-yl)acetylamino)-3-phenylpropionate hydrogen maleate

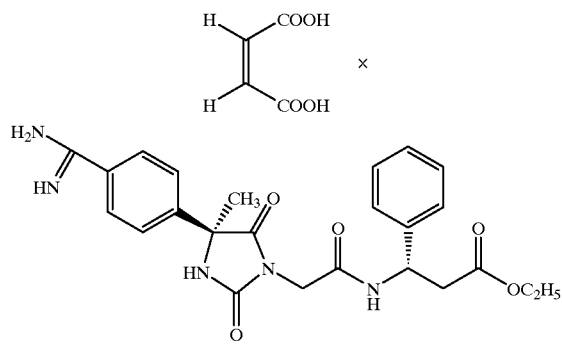

100 g of Amberlite® IRA93 (free base, Fluka) were stirred with 1000 ml of a 2M maleic acid solution at room temperature for 10 min. The maleic acid solution was sucked off and the ion exchange material was treated a further two times with 2M maleic acid solution in the same manner. The ion exchange resin was then washed with water until neutral. 1.51 g (3 mmol) of ethyl (S)-3-(2-((S)-4-(4-(amino-iminomethyl)phenyl)-4-methyl-2,5-dioxoimidazolidin-1-yl)acetylamino)-3-phenylpropionate hydrochloride were dissolved in 15 ml of water. The solution was allowed to run through an ion exchange column which was filled with 80 ml of Amberlite® IRA93 which had been loaded with maleic acid as described above. The column was then eluted with water. Fractions of 25 ml each were collected. Pure ethyl (S)-3-(2-((S)-4-(4-(amino-imino-methyl)phenyl)-4-methyl-2,5-dioxoimidazolidin-1-yl)acetylamino)-3-phenylpropionate hydrogen maleate crystallized out, at room temperature, from fractions 2 and 3. The crystals were isolated by filtration.

Yield: 771 mg of a white, crystalline solid (44%).
M.p. 228° C.
$[\alpha]_D = -54.4°$ (c=1; methanol; 22° C.)
FAB-MS: 466 (M+H)$^+$ An X-ray crystal structure analysis confirmed that the compound is ethyl (S)-3-(2-((S)-4-(4-(amino-imino-methyl)phenyl)-4-methyl-2,5-dioxoimidazolidin-1-yl)-acetylamino)-3-phenylpropionate hydrogen maleate (having an ethyl ester: maleic acid ratio of 1:1), which can also be represented by the following ionic formula which is equivalent to the above formula.

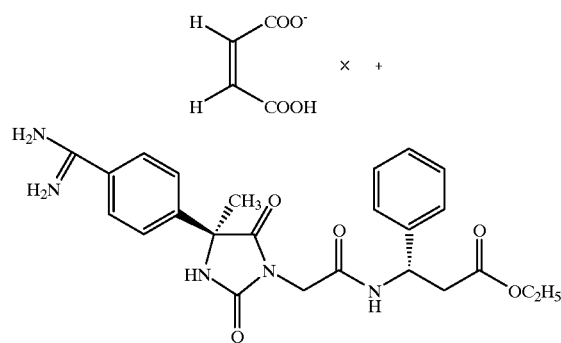

A further 740 mg of pure ethyl (S)-3-(2-((S)-4-(4-(amino-imino-methyl)-phenyl)-4-methyl-2,5-dioxoimidazolidin-1-yl)acetylamino)-3-phenyl-propionate hydrogen maleate could be isolated from the mother liquors of fractions 2 and 3, and from fractions 4 to 12, by means of freeze-drying the aqueous solution.
Total yield: 1.511 g (87%).

Example 2

Ethyl (S)-3-(2-( (S)-4-(4-(amino-imino-methyl)phenyl)-4-methyl-2,5-dioxo-imidazolidin-1-yl)acetylamino)-3-phenylpropionate hydrogen maleate 2a. Ethyl (S)-3-(2-((S)-4-(4-cyanophenyl)-4-methyl-2,5-dioxo-imidazolidin-1-yl)acetylamino)-3-phenylpropionate 7.7 kg (33.5 mol) of ethyl (S)-3-amino-3-phenylpropionate hydrochloride were initially introduced into a vessel, and a solution of 9.14 kg (33.5 mol) of 2-(S)-4-(4-cyanophenyl)-4-methyl-2,5-dioxoimidazolidin-1-yl)acetic acid in 50 l of ethyl acetate was added. 7.72 kg (8.54 l; 67 mol) of N-ethylmorpholine were pumped in at an internal temperature of from 20 to 23° C. The mixture was stirred for 15 min, after which 11 kg (33.5 mol) of O-((cyano(ethoxycarbonyl)methylene)amino-N,N,N',N'-tetramethyluronium tetrafluoroborate (TOTU) were introduced, by way of an entry lock, in one portion at from 20 to 23° C. The mixture was subsequently stirred at a temperature of from 20 to 23° C. for 2 h, after which 50 l of water were added and the mixture was stirred at a temperature of from 20 to 23° C. for 30 min. 50 l of methyl tert-butyl ether were added and the mixture was subsequently stirred at a temperature of from 8 to 12° C. for 2 h. The white suspension was transferred to a centrifuge and centrifuged. The filter cake was washed with 28 l of water, then with 28 l of ethanol and finally with a further 56 l of water. The product was dried in a vacuum drying oven at 40° C. in a stream of nitrogen.

Yield: 9.84 kg (85%).

FAB-MS: 449 (M+H)$^+$

2b. Ethyl (S)-3-(2-((S)-4-(4-(amino-hydroximino-methyl) phenyl)-4-methyl-2,5-dioxoimidazolidin-1-yl) acetylamino)-3-phenylpropionate b 120l of ethanol were initially introduced into a vessel. At room temperature, 12 kg (26.786 mol) of ethyl (S)-3-(2-((S)-4-(4-cyanophenyl)-4-methyl-2,5-dioxoimidazolidin-1-yl)acetylamino)-3 -phenylpropionate were added into the vessel, while stirring. 3.74 kg (53.813 mol) of hydroxylamine hydrochloride and 5.44 kg (7.45 l; 53.86 mol) of triethylamine were added. The reaction mixture was heated to reflux and stirred at 80° C. for 2 h. 90 l of ethanol were distilled off in vacuo at a bath temperature of 50° C. The remaining mixture was taken up in 220 l of ethyl acetate and this latter mixture was extracted three times with 50 l of water on each occasion. The ethyl acetate phase was evaporated down to 30 l in vacuo and at a bath temperature of 50° C. It was treated four times with 10 l of toluene on each occasion and evaporated to dryness.

Yield: 11.1 kg (85%).

FAB-MS: 482 (M+H)$^+$

2c. Ethyl (S)-3-(2-((S)-4-(4-(amino-imino-methyl)phenyl)-4-methyl-2,5-dioxoimidazolidin-1-yl)acetylamino)-3-phenylpropionate acetic acid salt 11 kg (22.869 mol) of ethyl (S)-3-(2-((S)-4-(4-(amino-hydroximino-methyl)-phenyl)-4-methyl-2,5-dioxoimidazolidin-1-yl)acetylamino)-3-phenyl-propionate were dissolved in 70 l of glacial acetic acid and this solution was introduced into a 125 l autoclave. A suspension of 1.0 kg of palladium/charcoal (10%; 50% water) and 5 l of glacial acetic acid was added to the solution. The mixture was hydrogenated for 15 h at 50° C. and 10 bar hydrogen pressure. The catalyst was filtered off with suction through a pressure filter under nitrogen and washed with 5 l of glacial acetic acid. The filtrate was completely evaporated in vacuo on a rotary evaporator at a bath temperature of 60° C. The residue was dissolved in 30 l of acetone and the solution was added, over 30 min and at 20° C., to 200 l of methyl tert-butyl ether. The mixture was subsequently stirred at room temperature for 1 h and the precipitated product was centrifuged. The filter cake was subsequently washed with 10 l of methyl tert-butyl ether, removed from the centrifuge and dried in vacuo. 10.1 kg (85%) of product were obtained.

FAB-MS: 466 (M+H)$^+$

For purification, 90 l of acetone were initially introduced into a vessel and 10.1 kg of the above product were added. The mixture was heated to 50° C. and stirred for 1 h. Stirring was then continued overnight at a jacket temperature of 20° C., after which the solid was isolated using a centrifuge. It was washed with 10 l of acetone. The acetone-moist product was stirred up with 50 l of acetone and heated to reflux temperature (57° C.) and stirred for 1 h. The mixture was allowed to cool down over 24 h and while stirring; it was then stirred at 15° C. for 1 h and the product was isolated using a centrifuge. The filter cake was washed with 10 l of methyl tert-butyl ether, removed from the centrifuge and dried in vacuo at 0.1 bar and 40° C. The product was milled.

Yield: 7.2 kg (60%).

FAB-MS: 466 (M+H)$^+$

2d. Ethyl (S)-3-(2-( (S)-4-(4-(amino-imino-methyl) phenyl)-4-methyl-2,5-dioxoimidazolidin-1-yl)-acetylamino)-3-phenylpropionate hydrogen maleate 75.68 g (144 mmol) of ethyl (S)-3-(2-((S)-4-(4-(amino-imino-methyl) phenyl)-4-methyl-2,5-dioxoimidazolidin-1-yl)-acetylamino)-3-phenylpropionate acetic acid salt were dissolved in 340 ml of water. The solution was filtered, and a solution of 16.87 g (144 mmol) of maleic acid (99%) in 48 ml of water was added while stirring. The mixture was stirred at room temperature for 1 h and was subsequently left to stand overnight in an ice bath. The product precipitated out of the solution as a crystalline solid. It was filtered off with suction and dried under high vacuum over phosphorus pentoxide.

Yield: 80.7 g of a white, crystalline solid (96%).

M.p. 228° C.

$[\alpha]_D$=−54.4° (c=1; methanol; 22° C.)

FAB-MS: 466 (M+H)$^+$

Preparation of the starting compounds which are employed in step 2a

I. Ethyl (S)-3-amino-3-phenylpropionate hydrochloride

Ia. (R)-2-Amino-2-phenylethanol 20 g (920 mmol) of lithium borohydride were dissolved in 420 ml of absolute tetrahydrofuran. 233.5 ml (1.84 mol) of trimethylchlorosilane were added dropwise, while stirring, and 69.5 g (0.46 mol) of (R)-phenylglycine were subsequently added in portions over a period of 4 hours. The reaction mixture was stirred at room temperature overnight. 690 ml of methanol were then added and the mixture was stirred at room temperature for 2 hours and concentrated in vacuo. The residue was dissolved, while stirring, in 690 ml of a 20% aqueous solution of potassium hydroxide. The aqueous phase was extracted three times with ethyl acetate. The combined organic phases were washed with water, dried over magnesium sulfate and concentrated in vacuo.

Yield: 41.2 g (65.3 %).

FAB-MS: 138 (M+H)$^+$

Ib. (R)-2-Benzyloxycarbonylamino-2-phenylethanol 40.5 g (295 mol) of (R)-2-amino-2-phenylethanol were dissolved in 385 ml of absolute dimethylformamide. 73.5 g of N-(benzyloxycarbonyloxy)-succinimide (295 mmol) were added, at 0° C. and while stirring, and the mixture was stirred at 0° C. for 1 hour. The ice bath was removed and the mixture was left to stand at room temperature for 48 h. The reaction solution was concentrated in vacuo and the residue was subsequently taken up in 500 ml of ethyl acetate. The organic phase was washed twice with a 10% aqueous solution of citric acid and once with water. It was dried over anhydrous sodium sulfate and concentrated. The resulting crystalline crude product (82.3 g) was dissolved once again in ethyl acetate. The organic phase was washed twice with a 10% aqueous solution of citric acid and once with water. Recrystallization subsequently took place from ethyl acetate/petroleum ether.

Yield: 74.6 g (93.3 %).

FAB-MS: 272 (M+H)$^+$

Ic. ((R)-2-Benzyloxycarbonylamino-2-phenylethyl) 4-methylphenylsulfonate 53.9 g of (R)-2-benzyloxycarbonylamino-2-phenylethanol (198.7 mmol) were dissolved in a mixture of 500 ml of methylene chloride and 80.3 ml (993.5 mmol) of pyridine. 45.5 g (238.4 mmol) of tosyl chloride in 240 ml of methylene chloride were added, at 0° C. and while stirring, and the mixture was left to stir at room temperature for 7 hours. A further 11.36 g of tosyl chloride (59.61 mmol) were added. The mixture was left to stir at 0° C. for 5 hours. It was then left to stand at room temperature overnight and subsequently concentrated in vacuo. The residue was taken up in ethyl acetate. The organic phase was washed three times with a 10% aqueous solution of citric acid and twice with water, dried over magnesium sulfate and concentrated in vacuo. The residue was triturated with diethyl ether, filtered off with suction, washed with diethyl ether and dried over phosphorus pentoxide. Yield: 60.9 g (72 %). The mother liquor was concentrated, and the residue was taken up in n-heptane/ethyl acetate (6 : 4) and chromatographed through silica gel.
Yield: 3.5 g (4.2 %).
Total yield: 64.4 g (76.2 %).
FAB-MS: 426 (M+H)$^+$ Id. (S)-3-Benzyloxycarbonylamino-3-phenylpropionitrile 60.5 g of ((R)-2-benzyloxycarbonylamino-2-phenylethyl) 4-methylphenylsulfonate (142.2 mmol) were dissolved in 675 ml of dimethylformamide. 13.9 g of potassium cyanide (213.3 mmol), 5.64 g of 18-crown-6 (21.33 mmol) and 520 mg of potassium iodide (3.13 mmol) were added and the mixture was stirred at 50° C. for 20 hours. The reaction solution was poured into 500 ml of ice water and this mixture was subsequently stirred at 0° C. for 5 hours. It was then filtered with suction and the precipitate was dissolved in ethyl acetate. The organic phase was washed three times with water, dried over magnesium sulfate and concentrated in vacuo. The residue was triturated with diethyl ether, filtered off with suction, washed with diethyl ether and dried over phosphorus pentoxide.
Yield: 25.3 g (63.5 %).
FAB-MS: 281 (M+H)$^+$ Ie. Ethyl (S)-3-benzyloxycarbonylamino-3-phenylpropionate 15 g of (S)-3-benzyloxycarbonylamino-3-phenylpropionitrile (53.51 mmol) were suspended in a mixture of 110 ml of absolute ethanol and 30 ml of dioxane. HCl gas was passed in, at 10–15° C. and while stirring and cooling. After a short time, a clear solution was formed. Further HCl gas was passed in, while cooling, until starting material could no longer be detected in a thin layer chromatogram. Nitrogen was then passed through the reaction solution for 15 minutes and the mixture was subsequently concentrated in vacuo. Water was added to the residue until persistent turbidity was obtained. The mixture was stirred at room temperature for 30 minutes and the aqueous phase was subsequently extracted three times with ethyl acetate. The combined organic phases were washed with water, dried over magnesium sulfate and concentrated in vacuo. The residue was taken up in ethyl acetate/petroleum ether (1: 1) and chromatographed through silica gel.
Yield: 10.55g (60%).
FAB-MS: 328 (M+H)$^+$ If. Ethyl (S)-3-amino-3-phenylpropionate hydrochloride 10.29 g of ethyl (S)-benzyloxycarbonylamino-3-phenylpropionate (31.44 mmol) were dissolved in 125 ml of ethanol and hydrogenated catalytically over Pd/active charcoal at a pH of 4 while adding 2N ethanolic HCl using an automatic burette. The catalyst was filtered off with suction through kieselguhr and the filtrate was concentrated. The residue was triturated with diethyl ether, filtered off with suction, washed with diethyl ether and dried over phosphorus pentoxide.
Yield: 5.05 g (70%).
FAB-MS: 194 (M+H)$^+$ II. 2-( (S)-4-(4-Cyanophenyl)-4-methyl-2,5-dioxoimidazolidin-1-yl)acetic acid IIa. (R,S)-4-(4-Bromophenyl)-4-methyl-2,5-dioxoimidazolidine 49.8 g (0.25 mol) of 4-bromoacetophenone, 21.2 g (0.325 mol) of potassium cyanide and 211.4 g (2.2 mol) of ammonium carbonate were suspended in 1.0 l of an aqueous solution of ethanol (0.5 l of distilled water and 0.5 l of ethanol). The suspension was stirred at 60° C. until starting material could no longer be detected by thin layer chromatography (8 hours). The mixture was allowed to cool down to room temperature. The pH of the solution was adjusted to 6.3 with half-concentrated hydrochloric acid. The product separated out as a white precipitate. The mixture was left to stand at 4° C. overnight. The white precipitate was filtered off with suction, washed with water and dried in vacuo over phosphorus pentoxide.
Yield: 65.3 g of a white solid (97%).
FAB-MS: 269 (M+H)$^+$ IIb. (R,S)-2-Amino-2-(4-bromophenyl)propionic acid 5.3 g (20 mmol) of (R,S)-4-(4-bromophenyl)-4-methyl-2,5-dioxoimidazolidine were suspended in 50 ml of 3 N sodium hydroxide solution. The suspension was heated at 145° C. for 1 hour in an autoclave at a nitrogen excess pressure of 10 bar. The cooled reaction solution was diluted with 150 ml of water and was brought to a pH of 4 with acetic acid while stirring vigorously and while cooling with ice. It was stirred at 0° C. for 2 hours. The precipitate was filtered off with suction, washed with water and dried in vacuo over phosphorus pentoxide.
Yield: 3.65 g of a white solid (75%).
FAB-MS: 244 (M+H)$^+$ IIc. Ethyl (R,S)-2-amino-2-(4-bromophenyl)propionate 27.3 g (112.3 mmol) of (R,S)-2-amino-2-(4-bromophenyl)propionic acid were suspended in 150 ml of 9.8N ethanolic hydrogen chloride solution. The mixture was heated under reflux for 18 hours, after which a further 50 ml of 9.8N ethanolic hydrogen chloride solution were added and the mixture was heated under reflux for a further 5 hours. The solution was concentrated and the residue was partitioned between ethyl acetate and a saturated solution of sodium bicarbonate. The organic phase was washed with water and dried over sodium sulfate. For purification, the crude product (23.22 g) was distilled under high vacuum (boiling point=129–130° C. at 2 mm Hg).
Yield: 20.7 g (68%).
FAB-MS: 272 (M+H)$^+$ IId. Ethyl (S)-2-amino-2-(4-bromophenyl)propionate 44.3 g (1 63 mmol) of ethyl (R,S)-2-amino-2-(4-bromophenyl)propionate and 24.8 g of D-(−)-mandelic acid (163 mmol) were dissolved, at room temperature, in 138 ml of isopropanol. 414 ml of diisopropyl ether were added and the mixture was cooled at 0° C. overnight. The precipitate which had separated out was filtered off with suction. The resulting salt was then recrystallized two further times in the same manner. 20 g of enantiomerically pure salt were obtained ($[\alpha]_D$=−14° (c=1, 2.15N ethanolic hydrogen chloride solution; 22° C.). The salt was partitioned between ethyl acetate and an aqueous solution of sodium bicarbonate. The organic phase was washed with water, dried over magnesium sulfate and concentrated in vacuo. After derivatizing with R-(−)-α-methoxy-α-(trifluoromethyl)phenylacetyl chloride (Mosher reagent), the enantiomeric purity was determined by HPLC to be greater than 99% ee.
Yield: 12.5 g (28%).
$[\alpha]_D$=+52.7' (c=1; 2.15 N ethanolic hydrogen chloride solution; 22° C.)
FAB-MS: 272 (M+H)$^+$ IIe. N-((S)-1-(4-Bromphenyl)-1-(ethoxycarbonyl)ethyl)-N'-(ethoxycarbonyl methyl)urea 12.4 g (45.6 mmol) of ethyl (S)-2-amino-2-(4-bromophenyl)propionate were dissolved in 70 ml of methylene chloride. A solution of 5.11 ml (45.6 mmol) of ethyl isocyanatoacetate in 35 ml of methylene chloride was added dropwise at 0° C. and over a period of 15 minutes. The mixture was stirred at 0° C. for 2 hours and then concentrated.

Yield: 18.1 g (99%).
$[\alpha]_D$=+10.7° (c=1; 2.15 N ethanolic hydrogen chloride solution; 22° C.)
FAB-MS: 401 (M+H)$^+$ IIf. 2-((S)-4-(4-Bromophenyl)-4-methyl-2,5-dioxoimidazolidin-1-yl)acetic acid 180 ml of a 6 N solution of hydrochloric acid were added to 18 g (44.9 mmol) of N-((S)-1-(4-bromophenyl)-1-(ethoxycarbonyl)ethyl)-N'-(ethoxy-carbonylmethyl)urea. The reaction mixture was heated to boiling under reflux for 10 hours. It was allowed to cool down to 0° C. and the precipitated reaction product was filtered off with suction, subsequently washed with water and dried in vacuo over phosphorus pentoxide.
Yield: 11.4 g (78%).
$[\alpha]_D$=+32.8° (c=1; 2.15 N ethanolic hydrogen chloride solution; 22° C.)
FAB-MS: 327 (M+H)$^+$ IIg. 2-((S)-4-(4-Cyanophenyl)-4-methyl-2,5-dioxoimidazolidin-1-yl)acetic acid 11.75 g (35.9 mmol) of 2-((S)-4-(4-bromophenyl)-4-methyl-2,5-dioxoimidazolidin-1-yl)acetic acid were dissolved in 90 ml of dimethylformamide. 14.15 g (158 mmol) of copper(I) cyanide were added and the mixture was heated under reflux for 20 hours while being stirred. The reaction mixture was cooled down and then poured into 300 ml of water. The aqueous phase was rendered acidic (pH=1–1.5) with concentrated hydrochloric acid, stirred for 30 minutes and filtered with suction through a Seitz layer. The aqueous phase was extracted three times with ethyl acetate. The combined organic phases were washed with water, dried over magnesium sulfate and concentrated in vacuo.
Yield: 9.3 g (95%).
$[\alpha]_D$=+33.4° (c=1; 2.15 N ethanolic hydrogen chloride solution; 22° C.)
FAB-MS: 274 (M+H)$^+$ Example 3

Determination of Water Vapor Sorption

The water uptake of a substance was determined using an automatic two-limbed microbalance which is operated in vacuo or in an atmosphere which has a defined composition or a defined pressure. The dry sample is located on one side of the balance and a taring weight is located on the other side. A water vapor atmosphere, whose pressure was increased stepwise, was generated in the weighing space. The increase in weight of the sample as a function of the water vapor pressure was recorded. The measurement was carried out at a constant temperature of 25° C.

The weighing space was first of all evacuated to constant weight and the starting weight of the sample was determined. A defined quantity of water vapor was then passed into the evacuated weighing space through an inlet valve. In the experiment which is reproduced below, the water vapor pressure which was set in this first step corresponds, at the measuring temperature of 25° C., to a relative atmospheric humidity of 4.7%. When constant weight was once again reached after passing in the water vapor, i.e. when the sample was in equilibrium with the water vapor atmosphere, the increase in weight of the sample was recorded. After that, the water vapor pressure was increased in several steps by passing in further water vapor (with each water vapor pressure corresponding to a defined relative atmospheric humidity at the measuring temperature of 25° C.). In each step, the increase in weight of the sample was recorded after constant weight had been reached. When ethyl (S)-3-(2-((S)-4-(4-(amino-imino-methyl)phenyl)-4-methyl-2,5-dioxoimidazolidin-1-yl)-acetylamino)-3-phenylpropionate hydrogen maleate was examined, the following weight increases, based on the starting weight of the sample, were observed.

Relative Humidity 4.7% 18.5% 32.8% 49.6% 64.7% 75.5% 82.1%

Increase in 0.06% 0.11% 0.16% 0.23% 0.33% 0.43% 0.54% weight of the sample

The results demonstrate that, even at a relative atmospheric humidity of approx. 80%, the increase in weight of ethyl (S)-3-(2-((S)-4-(4-(amino-imino-methyl)phenyl)-4-methyl-2,5-dioxoimidazolidin-1-yl)acetylamino)-3-phenylpropionate hydrogen maleate is only very slight (approx. 0.5%); thus, the substance is not hygroscopic.

Example 4

Pharmacological Investigation in the Model Coronary Cyclic Flow Variations in Dogs (Model of Unstable Angina)

Dogs of either sex (20–35 kg) were anesthetized (Ketamine plus sodium pentobarbital infusion), ventilated and instrumented for the measurement of hemodynamic parameters (peripheral and left ventricular blood pressure, myocardial contractility, heart rate), and ECG. Blood gases and hematocrit were kept constant by infusion of electrolytes. After a left thoracotomy, the heart was exposed and the left circumflex coronary artery (LCX) was instrumented with an electromagnetic flow probe to measure mean coronary blood flow. Distal to the flow probe, the LCX was shortly squeezed with forceps in order to damage the endothelium, and a small concentrically constricting plastic cylinder was placed onto the damaged site (between 1.0 and 1.7 mm inner diameter, depending on the size of the LCX, and 4 mm length). The constrictor abolished the reactive hyperemic response to a 10 second occlusion of the LCX and initiated the appearance of flow cycles (approx. 10 per hour) resulting from recurrent formation of platelet rich thrombi at the stenosed site. After 60 min of regular cyclic flow variations, the test compounds were administered by intravenous or intraduodenal bolus application. Cyclic flow variations were further monitored for at least 2 to 5 hours. Percent inhibition of coronary thrombotic cyclic flow variations was calculated by comparison of the mean number of cyclic flow variations per hour before and after administration of the compound in 5 to 8 animals. In control animals, the number of cyclic flow variations per hour remained constant for several hours. (References: Folts, J. D. et al. (1976), Circulation 54: 365–370; Just, M. et al. (1989), J. Cardiovasc. Pharmacol. 14 (suppl. 11): S 129–136)

When ethyl (S)-3-(2-((S)-4-(4-(amino-imino-methyl)phenyl)-4methyl-2,5-dioxoimidazolidin-1-yl)acetylamino)-3-phenylpropionate hydrogen maleate was examined the following results were obtained. Given is the percent reduction of the number of stenosis induced coronary cyclic flow variations (CFV's) per hour in the first, the second and the third hour after administration of the test compound as compared to the predrug period. The dose is given in mg per kg of body weight.

| Dose | | Reduction of CFV's (%) | | |
| --- | --- | --- | --- | --- |
| (mg/kg) | Administration | first hour | second hour | third hour |
| 0.1 | intravenuosly | 52 | 81 | 89 |
| 0.2 | intravenuosly | 75 | 96 | 99 |
| 0.1 | intraduodenally | 39 | 62 | 74 |
| 0.3 | intraduodenally | 23 | 66 | 78 |

The results obtained in this in vivo model demonstrate the powerful antithrombotic activity of the test substance, especially its coronary antithrombotic efficacy. All hemodynamic parameters record ed during the test were not significantly changed.

Example 5

Pharmacological Investigation in the Model ex vivo Platelet Aggregation Inhibition in Dogs Dogs of either sex (mixed breed of Labrador/Harrier, body weight 21–28 kg) were fasted overnight. The test compounds were administered orally in gelatine capsules or intravenously. Before administration of the test compounds and several times during 24 hours thereafter, 20 ml of blood were withdrawn from the cephalic vein into acid citrate dextrose (9+1volumes). Platelet rich plasma (PRP) was obtained by centrifugation. Platelet aggregation was measured in PRP after addition of either ADP (3–30 μmol/l) or collagen (0.3–10 μg/ml) plus epinephrine (10 μM) at 37° C. in an aggregometer (BioData). Percent of maximal aggregation before and after drug administration was compared. The percent inhibition of aggregation at the lowest concentration of the agonist which induced irreversible maximal aggregation is given. In addition, the cutaneous bleeding time was measured at the shaved inner forearm using the Simplate® 1 device at the times of blood collection. Percent prolongation of bleeding time after drug administration as compared to the predrug value is calculated.

When ethyl (S)-3-(2-( (S)-4-(4-(amino-imino-methyl) phenyl)-4-methyl-2,5-dioxoimidazolidin-1-yl) acetylamino)-3-phenylpropionate hydrogen maleate was examined the following results were obtained. Given is the percent inhibition of platelet aggregation 1 h, 4 h, 8 h and 24 h after administration of the test substance. The dose is given in mg per kg body weight. n is the number of dogs tested.

a) Inhibition of ADP-induced ex vivo platelet aggregation

| Dose | Administration | Inhibition of aggregation (%) | | | |
| --- | --- | --- | --- | --- | --- |
| (mg/kg) | (n) | after 1 h | after 4 h | after 8 h | after 24 h |
| 0.5 | intravenously (6) | 93 | 88 | 59 | 16 |
| 0.5 | orally (6) | 46 | 83 | 33 | 18 |
| 1 | orally (6) | 76 | 97 | 86 | 70 |
| 2 | orally (8) | 64 | 86 | 78 | 49 | a) Inhibition of collagen induced ex vivo platelet aggregation

| Dose | Administration | Inhibition of aggregation (%) | | | |
| --- | --- | --- | --- | --- | --- |
| (mg/kg) | (n) | after 1 h | after 4 h | after 8 h | after 24 h |
| 0.5 | intravenously (6) | 27 | 26 | 18 | 0 |
| 0.5 | orally (6) | 8 | 19 | 5 | 0 |
| 1 | orally (6) | 36 | 67 | 50 | 11 |
| 2 | orally (8) | 28 | 65 | 60 | 20 |

The maximal changes in bleeding time were 68% ($p<0.05$) prolongation at 4 hours after intravenous administration of 0.5 mg/kg and 122% ($p<0.05$) prolongation at 2 hours after oral administration of 2 mg/kg. At the lower oral doses, bleeding times were not significantly changed. The results of this test demonstrate the pronounced efficacy of the test substance as an in viva inhibitor of platelet aggregation.

It should be understood that the above described embodiments of the invention are illustrative only, and that modifications thereof may occur to those skilled in the art. Accordingly, the present invention is intended to embrace all such alternatives, modifications and variances which fall within the scope of the appended claims.

What is claimed is:

1. An ethyl 3-(2-(4-(4-(amino-imino-methyl)phenyl)-4-methyl-2,5-dioxo-imidazolidin-1-yl)acetylamino)-3-phynylpropionate hydrogen maleate of the formula I,

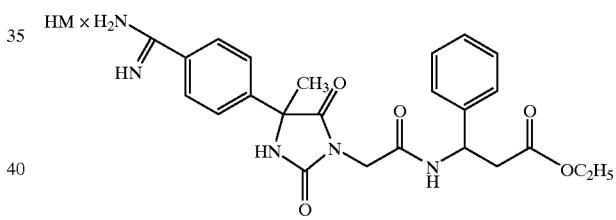

(I)

in which HM is maleic acid, in any stereoisomeric form, or mixtures thereof in any ratios, or a physiologically tolerated salt thereof.

2. A compound of the formula I as claimed in claim 1, wherein the (S) configuration is present at the chiral center in the imidazolidine ring and the (S) configuration is present at the chiral center in the propionic acid unit, or a physiologically tolerated salt thereof.

3. Ethyl (S)-3-(2-((S)-4-(4-(amino-imino-methyl) phenyl)-4-methyl-2,5-dioxo-imidazolidin-1-yl) acetylamino)-3-phenylpropionate hydrogen maleate.

4. A pharmaceutical composition for inhibiting thrombocyte aggregation which comprises an effective amount of at least one compound of the formula I as claimed in claim 1, or a physiologically tolerated salt thereof, as the active compound, and an inert carrier.

* * * * *